United States Patent [19]

Bourzat et al.

[11] 4,271,156
[45] Jun. 2, 1981

[54] PERHYDRO-1,3-THIAZINE DERIVATIVES

[75] Inventors: Jean-Dominique Bourzat, Paris; Daniel Farge, Thiais; Andre Leger, Paris; Gerard Ponsinet, Sucy-en-Brie, all of France

[73] Assignee: Rhone-Poulenc Industries, Paris, France

[21] Appl. No.: 94,335

[22] Filed: Nov. 14, 1979

[30] Foreign Application Priority Data

Nov. 16, 1978 [FR] France .................. 78 32387

[51] Int. Cl.³ .................. A61K 31/44; C07D 213/71; C07D 409/04
[52] U.S. Cl. .................. 424/246; 424/263; 544/54; 546/304; 546/305
[58] Field of Search .................. 544/54; 546/305, 304; 424/263, 246

[56] References Cited

U.S. PATENT DOCUMENTS

| | | | |
|---|---|---|---|
| 2,789,114 | 4/1957 | Fischback et al. | 546/305 |
| 2,909,460 | 10/1959 | Gaertner | 544/54 |
| 3,726,880 | 4/1973 | Capps | 546/305 |
| 3,732,216 | 5/1973 | Weinstock | 544/54 |
| 4,164,579 | 8/1979 | Bourzat et al. | 546/305 |

OTHER PUBLICATIONS

Knott, Chem. Abstracts, vol. 51, cols. 408–409 (1957).
Foye et al., Chem. Abstracts, vol. 52, col. 20154 (1958).
Knott, Chem. Abstracts, vol. 53, col. 946 (1959) (abst. of USP 2,839,404).

*Primary Examiner*—John D. Randolph
*Attorney, Agent, or Firm*—Stevens, Davis, Miller & Mosher

[57] ABSTRACT

Compounds of the general formula:

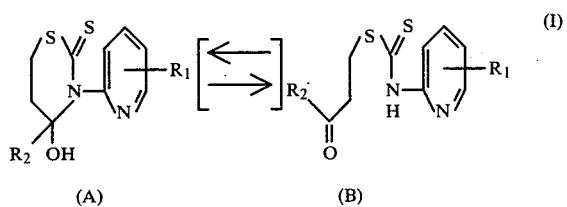

wherein $R_1$ represents hydrogen or halogen in the 4-, 5- or 6-position of the pyridyl radical and $R_2$ represents hydrogen, straight- or branched-chain alkyl of 1 to 4 carbon atoms or phenyl, possess anthelmintic activity, having a broad spectrum of activity against nematodes.

25 Claims, No Drawings

PERHYDRO-1,3-THIAZINE DERIVATIVES

DESCRIPTION

This invention relates to perhydro-1,3-thiazine derivatives, a process for their preparation and therapeutic compositions containing them.

The perhydro-1,3-thiazine derivatives of the present invention are those compounds of the general formula:

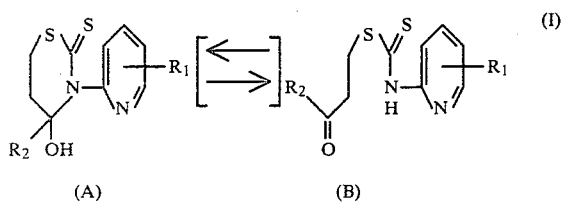

wherein $R_1$ represents a hydrogen or halogen atom in the 4-, 5- or 6-position of the pyridyl radical and $R_2$ represents a hydrogen atom, a straight- or branched-chain alkyl radical containing from 1 to 4 carbon atoms or a phenyl radical.

The products according to the invention can be in one of the forms I(A) or I(B) or an equilibrium mixture of these two forms, depending on internal parameters (in particular the radicals $R_1$ and $R_2$) or external parameters (in particular the presence of a solvent), as will be shown below.

The general formula I(A) corresponds to the preponderant form, in the crystalline state, of the products in which the symbol $R_1$ represents a hydrogen or halogen atom in the 4-, 5- or 6-position of the pyridyl radical and the symbol $R_2$ represents a hydrogen atom.

The general formula I(B) corresponds to the preponderant form, in the crystalline state, of the products in which the symbol $R_1$ represents a hydrogen or halogen atom in the 4-, 5- or 6-position of the pyridyl radical and the symbol $R_2$ represents a straight- or branched-chain alkyl radical containing from 1 to 4 carbon atoms or a phenyl radical.

According to a feature of the invention, the compounds of general formula I are prepared by reacting a compound of the general formula:

$$R_2-CO-R_3 \qquad \text{II}$$

wherein $R_2$ is as hereinbefore defined and $R_3$ represents a vinyl, 2-bromoethyl, 2-chloroethyl or 2-trimethylammonioethyl radical (the 2-trimethylammonioethyl radical being in the form of a salt, for example the chloride, bromide, iodide or methanesulphonate), with a dithiocarbamate of the general formula:

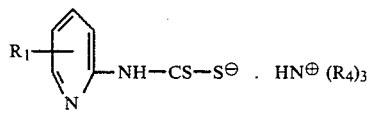

wherein $R_1$ is as hereinbefore defined and the symbols $R_4$ (which are identical or different) each represent an alkyl radical containing 1 to 4 carbon atoms.

The reaction is generally carried out in an organic solvent (for example chloroform, dimethylformamide or acetonitrile), in water or in an aqueous-organic medium (for example, in a mixture of water and dimethylformamide or water and acetonitrile), at a temperature from $-10°$ to $+50°$ C.

The dithiocarbamates of general formula III can be obtained, in accordance with the method described by E. B. Knott, J. Chem. Soc., 1644-9 (1956), by reacting carbon disulphide, in the presence of a tertiary amine, with a 2-aminopyridine of the general formula:

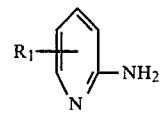

wherein $R_1$ is as hereinbefore defined, or in accordance with the method described by D. B. Capps in U.S. Pat. No. 3,726,880.

The compounds of general formula II can be obtained in accordance with the method described by C. W. Spangler, J. Org. Chem., 38, 3483 (1973), by applying the method described by F. F. Blicke and J. H. Burckhalter, J. Amer. Chem. Soc., 64, 451 (1942) or by applying the method described by A. N. Kost and V. V. Ershov, Zhur. Obshchei Khim., 27, 1722-26 (1957).

The perhydro-1,3-thiazine derivatives of general formula I can be purified, if necessary, by physical methods such as crystallisation or chromatography.

The perhydro-1,3-thiazine derivatives of general formula I are particularly active as anthelmintics, having a broad spectrum of activity against nematodes.

Their activity has been demonstrated, especially in mice, against *Nematospiroides dubius* at doses of between 5 and 200 mg/kg animal body weight, administered orally.

Furthermore, the majority of the products according to the invention have been found to be active against filariosis in cotton rats due to *Litomosoides carinii*, at doses of between 50 and 100 mg/kg animal body weight per day, administered orally, for a treatment lasting 5 consecutive days.

The toxicity to mice of the products according to the present invention, expressed as their 50% lethal dose ($LD_{50}$) is between 150 mg/kg animal body weight and more than 1,000 mg/kg animal body weight, administered orally.

Of particular interest are those compounds of general formula I wherein $R_1$ represents a halogen, preferably chlorine, atom in the 5-position of the pyridyl radical and $R_2$ is as hereinbefore defined or wherein $R_1$ and $R_2$ each represent a hydrogen atom.

The compounds of general formula I wherein the symbols $R_1$ and $R_2$ have the meanings given in the following Table, chlorine atoms represented by $R_1$ being in the 5-position of the pyridyl radical, are particularly preferred.

TABLE

| $R_1$ | $R_2$ |
| --- | --- |
| H | H |
| H | methyl |
| H | ethyl |
| H | t-butyl |
| Cl | H |
| Cl | methyl |
| Cl | ethyl |
| Cl | t-butyl |
| H | phenyl |

The compound wherein $R_1$ represents a chlorine atom and $R_2$ represents a methyl group (the compound of formula I(B) which is 3-oxobutyl 5-chloropyrid-2-yldithiocarbamate) is of particular interest.

The following Examples illustrate the present invention.

EXAMPLE 1

A solution of acrolein (19.5 g) in anhydrous acetonitrile (45 cc) is added to a suspension of triethylammonium pyrid-2-yldithiocarbamate (90.0 g) in anhydrous acetonitrile (450 cc) without allowing the temperature to exceed 10° C. The reaction is allowed to proceed for 1 hour without allowing the temperature to exceed 10° C. 2.3 N aqueous hydrochloric acid (144 cc) is then added without allowing the temperature to exceed 10° C. The crystals which appear are filtered off, washed twice with acetonitrile (total 50 cc) and three times with distilled water (total 120 cc) and dried under reduced pressure (20 mmHg) at 20° C. A first fraction (17.8 g) of a product melting at 115° C. is obtained. The filtrate is evaporated to dryness under reduced pressure (20 mmHg) at 45° C. The residue obtained is dissolved in methylene chloride (600 cc). The organic solution is washed four times with distilled water (total 600 cc), dried over sodium sulphate and the organic solvent evaporated off. The product obtained (50.0 g) is purified by recrystallisation from ethanol (150 cc). A second fraction (13.3 g) of a product melting at 113°–115° C. is obtained. The two fractions are combined and dissolved in boiling methylene chloride (170 cc); diethyl ether (170 cc) is added. After cooling for 3 hours at 2° C., the crystals which appear are filtered off, washed with a mixture of methylene chloride (15 cc) and diethyl ether (15 cc) and then twice with diethyl ether (60 cc) and dried under reduced pressure (0.2 mmHg) at 50° C. 4-Hydroxy-3-(pyrid-2-yl)-perhydro-1,3-thiazine-2-thione (23.0 g), which melts at 120° C., is thus obtained.

When the product is examined by IR (infrared) spectroscopy in chloroform solution, a band at 1,725 cm$^{-1}$ is observed which may correspond to a maximum of 5% of 2-formylethyl pyrid-2-yldithiocarbamate. This band is not observed when the product is examined between plates in petroleum jelly.

The triethylammonium pyrid-2-yldithiocarbamate (m.p.=95° C.) used as starting material is prepared in accordance with the method described by E. B. Knott, J. Chem. Soc., 1,644–9 (1956).

EXAMPLE 2

A solution of but-3-en-2-one (11.6 g) in anhydrous acetonitrile (15 cc) is added, at a maximum temperature of 5° C., to a suspension of triethylammonium pyrid-2-yldithiocarbamate (45.0 g) in anhydrous acetonitrile (280 cc). The reaction is allowed to proceed for 2 hours at a maximum temperature of 2° C. A 3.5 N solution of anhydrous hydrogen chloride in diethyl ether (47.5 cc) is added at a maximum temperature of 0° C. The triethylamine hydrochloride is filtered off and washed twice with a mixture of acetonitrile and diethyl ether (40 cc and 140 cc, respectively). The solvents are evaporated off under reduced pressure (20 mmHg) at 45° C. The residue is treated with diethyl ether (600 cc). The ethereal solution is washed twice with distilled water (total 240 cc), dried over sodium sulphate and the solvent evaporated off. The residue obtained (30.2 g) is dissolved in methylene chloride (120 cc), silica (0.2–0.5 mm; 25.0 g) is added and the solvent is then evaporated off. The silica impregnated with the product is introduced onto a column of diameter 4 cm, containing silica (0.2–0.5 mm; 300 g). Elution is carried out successively with a mixture of cyclohexane (1,600 cc) and ethyl acetate (400 cc) and then with a mixture of cyclohexane (375 cc) and ethyl acetate (125 cc) and the eluates are discarded. Elution is continued with a mixture of cyclohexane (1,800 cc) and ethyl acetate (600 cc). The eluate is collected and then evaporated to dryness under reduced pressure (20 mmHg) at 45° C. The crystals obtained (24.5 g; m.p. about 65° C.) are treated with a mixture of diisopropyl ether (60 cc) and diethyl ether (60 cc). The crystals are filtered off, washed successively with a mixture of diisopropyl ether (25 cc) and diethyl ether (25 cc) and then twice with diisopropyl ether (50 cc) and dried under reduced pressure (20 mmHg) at 40° C. 3-Oxobutyl pyrid-2-yldithiocarbamate (21.2 g) (structure determined by IR spectroscopy in petroleum jelly), which melts at 74° C., is thus obtained.

EXAMPLE 3

The procedure of Example 2 is followed but triethylammonium pyrid-2-yldithiocarbamate (54.0 g) and pent-1-en-3-one (17.0 g) in anhydrous acetonitrile (400 cc) are used as the starting materials at a maximum temperature of 5° C. The reaction is allowed to proceed for 3 hours at between 5° and 20° C. The crude product (45.0 g) is dissolved in a mixture of chloroform (200 cc) and ethyl acetate (50 cc). The solution is chromatographed on a column of diameter 6 cm, containing silica (0.063–0.2 mm; 600 g). Elution is carried out with a mixture of chloroform (400 cc) and ethyl acetate (100 cc), this eluate being discarded, and then with a mixture of chloroform (2,800 cc) and ethyl acetate (700 cc), this eluate being collected and evaporated to dryness under reduced pressure (20 mmHg) at 45° C. The product obtained (30.0 g) is purified by recrystallisation from a mixture of acetonitrile (30 cc) and diisopropyl ether (60 cc). 3-Oxopentyl pyrid-2-yldithiocarbamate (16.0 g) (structure determined by IR spectroscopy in petroleum jelly), which melts at 80° C., is obtained.

EXAMPLE 4

A solution of 2,2-dimethylpent-4-en-3-one (22.5 g) in anhydrous acetonitrile (50 cc) is added, at a maximum temperature of 5° C., to a suspension of triethylammonium pyrid-2-yldithiocarbamate (54.2 g) in anhydrous acetonitrile (150 cc). The reaction is allowed to proceed for 2 hours at between 5° and 20° C. The acetonitrile is evaporated off under reduced pressure (20 mmHg) at 45° C. The residue obtained is dissolved in methylene chloride (600 cc). The organic solution is washed four times with distilled water (total 600 cc), dried over sodium sulphate and evaporated. The product obtained (58.0 g) is dissolved in a mixture of chloroform (360 cc) and ethyl acetate (40 cc). The solution is chromatographed on a column of diameter 6 cm, containing silica (0.063–0.2 mm; 600 g). Elution is carried out with a mixture of chloroform (720 cc) and ethyl acetate (80 cc), this eluate being discarded, and then with a mixture of chloroform (3,000 cc) and ethyl acetate (350 cc), this eluate being collected and evaporated to dryness under reduced pressure (20 mmHg) at 45° C. The product obtained (42.0 g) is purified by recrystallisation from diisopropyl ether (200 cc). 4,4-Dimethyl-3-oxopentyl pyrid-2-yldithiocarbamate (36.0 g) (structure determined by IR spectroscopy in petroleum jelly), which melts at 95° C., is obtained.

The 2,2-dimethylpent-4-en-3-one (b.p. 0.5=65°-67° C.) used as starting material is prepared in accordance with the method described by C. W. Spangler, J. Org. Chem., 38, 3,483 (1973).

EXAMPLE 5

A solution of acrolein (17.6 g) in anhydrous acetonitrile (45 cc) is added, at a maximum temperature of 5° C., to a suspension of triethylammonium 5-chloropyrid-2-yldithiocarbamate (91.5 g) in anhydrous acetonitrile (450 cc). The reaction is allowed to proceed for 90 minutes at a maximum temperature of 5° C. The crystals which appear are filtered off, washed with ice-cooled acetonitrile (50 cc) and then four times with distilled water (total 480 cc) and dried in air. The product obtained (38.8 g; m.p.=136°-137° C.) is purified by recrystallisation from acetonitrile (240 cc). 3-(5-Chloropyrid-2-yl)-4-hydroxyperhydro-1,3-thiazine-2-thione (33.2 g), which melts at 141° C., is obtained.

When the product is examined by IR spectroscopy in chloroform solution, a band at 1,720 cm$^{-1}$ is observed which may correspond to a maximum of 5% of 2-formylethyl 5-chloropyrid-2-yldithiocarbamate. This band is not observed when the product is examined between plates in petroleum jelly.

The triethylammonium 5-chloropyrid-2-yldithiocarbamate (m.p.=130° C.) used as starting material is prepared in accordance with the method described by D. B. Capps in U.S. Pat. No. 3,726,880.

EXAMPLE 6

A solution of but-3-en-2-one (25.6 g) in anhydrous chloroform (90 cc) is added, at a maximum temperature of 5° C., to a suspension of triethylammonium 5-chloropyrid-2-yldithiocarbamate (110.0 g) in anhydrous chloroform (540 cc). The reaction is allowed to proceed for 1 hour at a maximum temperature of 5° C. A 3.7 N solution of hydrogen chloride in diethyl ether (97 cc) is added, at a maximum temperature of 0° C., and the mixture is then diluted with chloroform (500 cc). The chloroform solution is washed three times with distilled water (total 450 cc), dried over sodium sulphate and evaporated. The residue obtained (95.0 g) is dissolved in methylene chloride (300 cc), silica (0.2–0.5 mm; 60.0 g) is added and the solvent is then evaporated off. The silica impregnated with the product is introduced onto a column of diameter 7.5 cm, containing silica (0.2–0.5 mm; 900 g). Elution is carried out with a mixture of cyclohexane (6 liters) and ethyl acetate (1 liter), this eluate being discarded, and then with a mixture of cyclohexane (11.4 liters) and ethyl acetate (6.6 liters), this eluate being collected and evaporated to dryness under reduced pressure (20 mmHg) at 45° C. The product obtained (65.2 g; m.p. 116° C.) is purified by two successive recrystallisations from acetonitrile (210 cc) and then from a mixture of chloroform (250 cc) and diethyl ether (250 cc). 3-Oxobutyl 5-chloropyrid-2-yldithiocarbamate (47.5 g) (structure determined by IR spectroscopy in petroleum jelly), which melts at 120° C., is obtained.

EXAMPLE 7

The procedure of Example 6 is followed but triethylammonium 5-chloropyrid-2-yldithiocarbamate (91.5 g) and pent-1-en-3-one (28.0 g) in anhydrous chloroform (600 cc) are used as the starting materials at a maximum temperature of 5° C. The reaction is allowed to proceed for 2 hours at a maximum temperature of 5° C. The crude product (90.0 g) is dissolved in methylene chloride (400 cc). The solution is chromatographed on a column of diameter 6.5 cm, containing silica (0.063–0.2 mm; 750 g). Elution is carried out with methylene chloride (1,500 cc), this eluate being discarded, and then with methylene chloride (6 liters), this eluate being collected and evaporated to dryness. The product obtained (59.1 g) is purified by recrystallisation from a mixture of acetonitrile (60 cc) and diisopropyl ether (120 cc). 3-Oxopentyl 5-chloropyrid-2-yldithiocarbamate (49.0 g) (structure determined by IR spectroscopy in petroleum jelly), which melts at 80° C., is obtained.

EXAMPLE 8

A solution of 2,2-dimethylpent-4-en-3-one (30.0 g) in anhydrous acetonitrile (60 cc) is added, at a maximum temperature of 5° C., to a suspension of triethylammonium 5-chloropyrid-2-yldithiocarbamate (82.0 g) in anhydrous acetonitrile (400 cc). The reaction is allowed to proceed for 3 hours at between 5° and 20° C. The crystals which appear are filtered off; the filtrate is evaporated under reduced pressure (20 mmHg) at 45° C. The residue obtained and the crystals separated off beforehand are dissolved in methylene chloride (750 cc). The organic solution is washed four times with distilled water (total 600 cc), dried over sodium sulphate and evaporated. The product obtained (98.0 g) is dissolved in chloroform (400 cc). The solution is chromatographed on a column of diameter 6.8 cm, containing silica (0.063–0.2 mm; 800 g). Elution is carried out with chloroform (2.6 liters), this eluate being discarded, and then with chloroform (7.2 liters), this eluate being collected and evaporated to dryness. The product obtained (85.0 g) is purified by recrystallisation from acetonitrile (350 cc). 4,4-Dimethyl-3-oxopentyl 5-chloropyrid-2-yldithiocarbamate (70.0 g) (structure determined by IR spectroscopy in petroleum jelly), which melts at 111° C., is obtained.

EXAMPLE 9

4,4-Dimethyl-3-oxopentyltrimethylammonium iodide (6.0 g) is added, at 20° C., to a suspension of triethylammonium 5-chloropyrid-2-yldithiocarbamate (6.1 g) in anhydrous acetonitrile (25 cc). The reaction is allowed to proceed for 6 hours at 20° C. Distilled water (25 cc) is added. The crystals which appear are filtered off, washed three times with distilled water (total 30 cc) and dried in air at 20° C. The product obtained (5.1 g; m.p.=110° C.) is recrystallised from acetonitrile (15 cc). 4,4-Dimethyl-3-oxopentyl 5-chloropyrid-2-yldithiocarbamate (3.8 g), which melts at 111° C., is obtained.

The 4,4-dimethyl-3-oxopentyltrimethylammonium iodide (instantaneous m.p.=260° C.) used as starting material is prepared in accordance with the method described by A. N. Kost and V. V. Ershov, Zhur. Obshchei Khim., 27, 1,722-26 (1957).

EXAMPLE 10

The procedure of Example 4 is followed but a suspension of triethylammonium pyrid-2-yldithiocarbamate (81 g) in acetonitrile (400 cc) and a solution of 1-phenylprop-2-en-1-one (40 g) in acetonitrile (100 cc) are used as the starting materials at a maximum temperature of 25° C. The reaction is allowed to proceed for 4 hours at between 20° and 25° C. Triethylammonium pyrid-2-yldithiocarbamate (21 g) is filtered off. The acetonitrile is evaporated off under reduced pressure (20 mmHg) at 45° C. The residue is dissolved in chloroform (500 cc)

and the chloroform solution is washed three times with distilled water (total 300 cc), dried over sodium sulphate and evaporated to dryness. The product obtained (60 g) is dissolved in chloroform (400 cc); the solution is chromatographed on silica (0.063–0.2 mm; 600 g) distributed in a column of diameter 6 cm. Elution is carried out with chloroform (1,600 cc), this eluate being discarded, and then with chloroform (3,000 cc), this eluate being collected and evaporated to dryness under reduced pressure (20 mmHg) at 40° C. The chromatographed product (35.2 g) is purified by recrystallisation from diisopropyl ether (105 cc). 3-Oxo-3-phenylpropyl pyrid-2-yldithiocarbamate (25.5 g) (structure determined by IR spectroscopy in petroleum jelly), which melts at 120° C., is obtained.

The 1-phenylprop-2-en-1-one (b.p.=117°–118° C./20 mmHg) used as starting material is prepared in accordance with the method described by F. F. Blicke and J. H. Burckhalter, J. Amer. Chem. Soc., 64, 454 (1942).

The present invention also includes within its scope therapeutic compositions (for use in human or veterinary medicine) which comprise, as active ingredient, a derivative of general formula I in association with a pharmaceutically-acceptable carrier or coating. The invention includes especially such preparations made up for oral, parenteral or rectal administration. The pharmaceutical compositions of the invention may, if appropriate, contain other physiologically active products.

Solid compositions for oral administration include tablets, pills, e.g. sugar-coated pills, powders and granules. In such solid compositions the active compound is admixed with at least one inert diluent such as sucrose, lactose or starch. The compositions may also comprise, as is normal practice, additional substances other than inert diluents, e.g. lubricating agents, such as magnesium stearate. Liquid compositions for oral administration include pharmaceutically-acceptable emulsions, solutions, suspensions, syrups and elixirs containing inert diluents commonly used in the art, such as water and liquid paraffin. Besides inert diluents such compositions may also comprise adjuvants, such as wetting, emulsifying and suspending agents, and sweetening, flavouring and aromatizing agents. The compositions according to the invention, for oral administration, also include capsules of absorbable material such as gelatin containing the active substance with or without the addition of diluents or excipients.

Preparations according to the invention for parenteral administration include sterile suspensions or emulsions and aqueous or non-aqueous solutions. Examples of non-aqueous solvents or vehicles are propylene glycol, polyethylene glycol, vegetable oils such as olive oil, and injectable organic esters such as ethyl oleate. These compositions may also contain adjuvants such as preserving, wetting, emulsifying and dispersing agents. They may be sterilised by, for example, filtration through a bacteria-retaining filter, by incorporation in the compositions of sterilising agents, by irradiation, or by heating. They may also be manufactured in the form of sterile solid compositions, which can be dissolved in a sterile injectable medium immediately before use.

Compositions for rectal administration are suppositories which contain, in addition to the active substance, excipients such as cacao butter or a suitable wax base.

The percentage of active ingredient in the compositions of the invention may be varied, it being necessary that it should constitute a proportion such that a suitable dosage shall be obtained.

In the compositions of the invention, the active ingredient, when it is not dissolved, is advantageously in the micronised form.

The compounds according to the invention are useful an anthelmintics and the compositions of the invention may be used in human or veterinary medicine.

In veterinary medicine, the compounds of the invention can be used in the treatment of helminthiases caused by nematodes in cattle, sheep, horses and goats, at doses of from 5 to 50 mg/kg animal body weight, administered orally, for treatments lasting from 1 to 3 days, or at doses from 2.5 to 25 mg/kg animal body weight, over more prolonged periods as well as for the removal of gastrointestinal strongyles in sheep and intestinal nematodes in dogs.

In human medicine, the compounds of the invention can be used for removing anguillulae, ascarides and ankylostomes, in doses of from 5 to 50 mg/kg body weight, administered orally, for treatments lasting from 1 to 3 days.

The compounds of the invention can also be particularly useful in therapy in the treatment and prevention of human filarioses, namely cutaneo-dermic filarioses (onchocercosis, loasis and dracunculosis) and lymphatic filarioses (wuchereriasis and brugiasis).

In human therapy, the doses depend on the desired effect and the duration of the treatment; for an adult, they are generally from 10 to 50 mg/kg body weight per day, administered orally, and from 5 to 15 mg/kg body weight per day, administered intramuscularly, for treatments lasting from 1 to 30 days.

In general, the physician or veterinary surgeon will decide the posology considered appropriate as a function of the age, the weight and other factors perculiar to the subject to be treated.

The following Example illustrates compositions according to the invention.

EXAMPLE 11

Tablets containing 25 mg doses and having the following composition are prepared in accordance with the usual technique:
3-oxobutyl 5-chloropyrid-2-yldithiocarbamate: 25 mg
corn starch: 125 mg
colloidal silica: 45 mg
magnesium stearate: 5 mg

We claim:
1. A compound of the general formula:

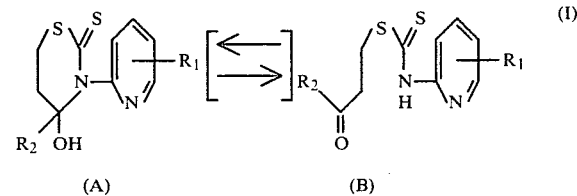

wherein $R_1$ represents hydrogen or halogen in the 4-, 5- or 6-position of the pyridyl radical and $R_2$ represents hydrogen, straight- or branched-chain alkyl of 1 to 4 carbon atoms or phenyl.

2. A compound according to claim 1 which, in preponderant form in the crystalline state, corresponds to general formula I(A) wherein the symbol $R_1$ represents hydrogen or halogen in the 4-, 5- or 6-position of the pyridyl radical and the symbol $R_2$ represents hydrogen.

3. A compound according to claim 1 which, in preponderant form in the crystalline state, corresponds to general formula I(B) wherein the symbol $R_1$ represents hydrogen or halogen in the 4-, 5- or 6-position of the pyridyl radical and the symbol $R_2$ represents straight- or branched-chain alkyl radical of 1 to 4 carbon atoms or phenyl.

4. A compound according to claim 1 wherein $R_1$ represents halogen in the 5-position of the pyridyl radical and $R_2$ is as defined in claim 1 or wherein $R_1$ and $R_2$ each represent hydrogen.

5. A compound according to claim 4 wherein $R_1$ represents chlorine in the 5-position of the pyridyl radical.

6. A compound according to claim 1 wherein $R_1$ and $R_2$ each represent hydrogen.

7. The compound according to claim 6 which is 4-hydroxy-3-(pyrid-2-yl)-perhydro-1,3-thiazine-2-thione.

8. a compound according to claim 1 wherein $R_1$ represents hydrogen and $R_2$ represents methyl.

9. The compound according to claim 8 which is 3-oxobutyl pyrid-2-yldithiocarbamate.

10. A compound according to claim 1 wherein $R_1$ represents hydrogen and $R_2$ represents ethyl.

11. The compound according to claim 10 which is 3-oxopentyl pyrid-2-yldithiocarbamate.

12. A compound according to claim 1 wherein $R_1$ represents hydrogen and $R_2$ represents t-butyl.

13. The compound according to claim 12 which is 4,4-dimethyl-3-oxopentyl pyrid-2-yldithiocarbamate.

14. A compound according to claim 1 wherein $R_1$ represents chlorine in the 5-position of the pyridyl radical and $R_2$ represents hydrogen.

15. The compound according to claim 14 which is 3-(5-chloropyrid-2-yl)-4-hydroxyperhydro-1,3-thiazine-2-thione.

16. A compound according to claim 1 wherein $R_1$ represents chlorine in the 5-position of the pyridyl radical and $R_2$ represents methyl.

17. The compound according to claim 16 which is 3-oxobutyl 5-chloropyrid-2-yldithiocarbamate.

18. A compound according to claim 1 wherein $R_1$ represents chlorine in the 5-position of the pyridyl radical and $R_2$ represents ethyl.

19. The compound according to claim 18 which is 3-oxopentyl 5-chloropyrid-2-yldithiocarbamate.

20. A compound according to claim 1 wherein $R_1$ represents chlorine in the 5-position of the pyridyl radical and $R_2$ represents t-butyl.

21. The compound according to claim 20 which is 4,4-dimethyl-3-oxopentyl 5-chloropyrid-2-yldithiocarbamate.

22. A compound according to claim 1 wherein $R_1$ represents hydrogen and $R_2$ represents phenyl.

23. The compound according to claim 22 which is 3-oxo-3-phenylpropyl pyrid-2-yldithiocarbamate.

24. A therapeutic composition useful as an anthelmintic or antifilarial which comprises, as active ingredient, an effective amount of a compound as claimed in claim 1 in association with a pharmaceutically-acceptable carrier, and optionally with other compatible and physiologically active products.

25. A method of treating or preventing a helminth or filarial infection which comprises administering to a mammal suffering from or subject to a said infection an effective amount of a compound as claimed in claim 1.

* * * * *